US008609897B2

(12) United States Patent
Daniels et al.

(10) Patent No.: US 8,609,897 B2
(45) Date of Patent: *Dec. 17, 2013

(54) TRIFLUOROMETHYLSULFONAMIDE GAMMA SECRETASE INHIBITOR

(75) Inventors: Matthew Daniels, Jamaica Plain, MA (US); Jed Hubbs, Cambridge, MA (US); Thomas Miller, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 11 days.

This patent is subject to a terminal disclaimer.

(21) Appl. No.: 13/145,190

(22) PCT Filed: Jan. 29, 2010

(86) PCT No.: PCT/US2010/022560
§ 371 (c)(1),
(2), (4) Date: Jul. 19, 2011

(87) PCT Pub. No.: WO2010/090954
PCT Pub. Date: Aug. 12, 2010

(65) Prior Publication Data
US 2011/0275719 A1    Nov. 10, 2011

Related U.S. Application Data

(60) Provisional application No. 61/150,575, filed on Feb. 6, 2009.

(51) Int. Cl.
*C07C 311/01* (2006.01)
*A61K 31/18* (2006.01)
(52) U.S. Cl.
USPC ............. 564/99; 564/98; 564/95; 564/80; 514/605; 514/601; 514/579
(58) Field of Classification Search
None
See application file for complete search history.

(56) References Cited

U.S. PATENT DOCUMENTS

| 5,916,925 | A | 6/1999 | Higuchi et al. | |
|---|---|---|---|---|
| 6,890,956 | B2 | 5/2005 | Churcher et al. | |
| 7,101,895 | B2 * | 9/2006 | Churcher et al. | 514/317 |
| 7,595,344 | B2 * | 9/2009 | Castro Pineiro et al. | 514/618 |
| 7,655,675 | B2 * | 2/2010 | Nadin et al. | 514/317 |
| 2011/0263580 | A1 * | 10/2011 | Miller | 514/226.5 |

OTHER PUBLICATIONS

"Studies to Investigate the in Vivo Therapeutic Window of the γ-Secretase Inhibitor N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide (LY411,575) in the CRND8 Mouse" by Hyde et al., J. Pharmacol. Exp. Ther. 319, 1133-43 (2006).*
PCT International Search Report dated Mar. 14, 2010, mailed on Mar. 24, 2010 for related International Application No. PCT/US2010/022560; 1 page.
Imbimbo, Alzheimer's Disease: gamma-secretase inhibitors: Drug Discovery Today: Therapeutic Strategies Psychiatric disorders, vol. 5. No. 3, Autumn 2008, Abstract, p. 172.

* cited by examiner

*Primary Examiner* — Anna Pagonakis
*Assistant Examiner* — Theodore R West
(74) *Attorney, Agent, or Firm* — Raynard Yuro; John Todaro; Susan Hess

(57) ABSTRACT

The present invention is directed to a novel trifluoromethylsulfonamide derivative which inhibits the processing of APP by the putative γ-secretase and thus is useful in the treatment or prevention of Alzheimer's disease. This compound possesses favorable pharmacokinetic properties in higher species (rhesus) and thus can be dosed on an intermittent dosing regiment (e.g., once weekly). When dosed on such a regiment the compound exhibits significant and continuous Aβ lowering without the manifestation of Notch associated gastrointestinal toxicity for extended periods, e.g., 7 days. Pharmaceutical compositions and methods of use are also included.

8 Claims, No Drawings

TRIFLUOROMETHYLSULFONAMIDE GAMMA SECRETASE INHIBITOR

CROSS REFERENCE TO RELATED APPLICATIONS

This application is the national stage application under 35 U.S.C. 371 of International Patent Application No.: PCT/US2010/022560, filed in the U.S. Receiving Office on Jan. 29, 2010, which claims the benefit of U.S. Provisional Application No. 61/150,575, filed Feb. 6, 2009. Each of the aforementioned PCT and Provisional applications is incorporated by reference in its entirety as if fully set forth herein.

BACKGROUND OF THE INVENTION

This invention relates to a novel compound for treating or preventing diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase (see Selkoe, *Physiol. Rev.*, 81(2), 741-766 (2001). Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by 3-secretase. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

The role of secretases, including that of γ-secretase, in the processing of amyloid precursor protein (APP) to form Aβ is well documented in the literature, and so inhibiting the processing of APP by γ-secretase is recognized as a likely means of treating or preventing AD and related conditions (a recent review of activity in this area is provided by Garofalo, *Expert Opin. Ther. Patents* (2008) 18(7), 693-703). However, attempts to develop such a treatment have been hampered by the fact that γ-secretase is active towards a number of different transmembrane proteins in addition to APP (for a review, see Pollack and Lewis, *Current Opinion in Investigational Drugs* (2005), 6(1), 35-47), with the result that inhibition of γ-secretase can lead to unwanted side effects as well as the desired interruption of APP processing. In particular, γ-secretase plays a crucial role in the Notch cell-signaling process, which itself plays a crucial role in cell-fate determination. The Notch receptor protein is a transmembrane protein which, in response to activation by the relevant ligand, undergoes intramembranous cleavage by γ-secretase, releasing the Notch intracellular domain (NICD) which can then migrate to the cell nucleus and modulate gene transcriptions (Pollack and Lewis, supra). An example of cell-fate determination influenced by Notch is the differentiation of proliferative epithelial cells in the gastro-intestinal (GI) tract, with the result that suppression of Notch processing leads to intestinal goblet cell metaplasia and severe GI toxicity (Searfoss et al, *J. Biol. Chem.* (2003), 278(46), 46107-46116; Wang et al, *J. Biol. Chem.* (2004), 279(13), 12876-12882; Milano et al, *Toxicological Sciences*, (2004), 82, 341-358; and Van Es et al, *Nature* (2005), 435, 959-963).

There is therefore a need for a means of inhibiting the processing of APP that has minimal effect on the processing of Notch. Although there are a few reports of γ-secretase inhibitors showing selectivity for APP processing over Notch processing (see Garofolo, supra; and Petit et al, *J. Neuroscience* (2003), 74, 370-377), none has so far led to a viable treatment for AD. Furthermore, the present investigators have found that certain compounds which show selectivity for APP processing over Notch processing in vitro can still cause GI toxicity in vivo, particularly when administered to higher species such as primates. There is therefore an ongoing need for improved methods for inhibiting APP processing without incurring significant Notch-related GI toxicity.

The present invention is directed to a novel trifluoromethylsulfonamide derivative which inhibits the processing of APP by the putative γ-secretase and thus is useful in the treatment or prevention of AD. This compound possesses pharmacokinetic properties in higher species (rhesus) which are favorable for dosing on an intermittent dosing regiment (e.g., once weekly). When dosed on such a regiment the compound exhibits significant and continuous Aβ lowering without the manifestation of Notch associated gastrointestinal toxicity for extended periods, e.g., 7 days.

SUMMARY OF THE INVENTION

The present invention is directed to a novel trifluoromethylsulfonamide derivative which inhibits the processing of APP by the putative γ-secretase and thus is useful in the treatment or prevention of Alzheimer's disease. This compound possesses favorable pharmacokinetic properties in higher species (rhesus) and thus can be dosed on an intermittent dosing regiment (e.g., once weekly). When dosed on such a regiment the compound exhibits significant and continuous Aβ lowering without the manifestation of Notch associated gastrointestinal toxicity for extended periods, e.g., 7 days. Pharmaceutical compositions and methods of use are also included.

DETAILED DESCRIPTION OF THE INVENTION

The invention encompasses a compound which is

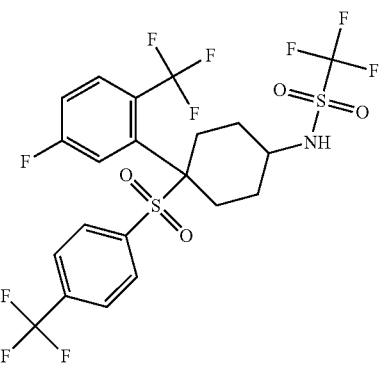 [SMILES: O=S(=O)(NC1CCC(c2cc(F)ccc2C(F)(F)F)(S(=O)(=O)c2ccc(C(F)(F)F)cc2)CC1)C(F)(F)F]

or a pharmaceutically acceptable salt thereof.

In an embodiment, the invention encompasses a compound which is

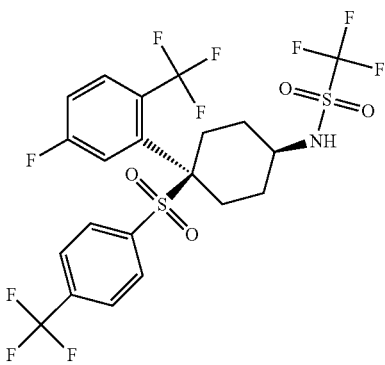 [SMILES: O=S(=O)(N[C@H]1CC[C@@](c2cc(F)ccc2C(F)(F)F)(S(=O)(=O)c2ccc(C(F)(F)F)cc2)CC1)C(F)(F)F]

or a pharmaceutically acceptable salt thereof.

In another embodiment, the invention encompasses a pharmaceutical composition comprising the compound described above or a pharmaceutically acceptable salt thereof and a pharmaceutically acceptable carrier.

In another embodiment, the invention encompasses a method for treating or preventing a disease involving deposition of β-amyloid (Aβ) in the brain which comprises administering to a human patient in need thereof the compound described above or a pharmaceutically acceptable salt thereof by an intermittent dosing regimen, the intermittent dosing regiment comprising repeating cycles of drug administration in which the compound is administered on one or more consecutive days followed by one or more consecutive days of rest on which the compound is not administered.

In another embodiment, the invention encompasses a method for treating or preventing Alzheimer's disease in a human patient in need thereof which comprises administering to the patient the compound described above or a pharmaceutically acceptable salt thereof by an intermittent dosing regimen, the intermittent dosing regiment comprising repeating cycles of drug administration in which the compound is administered on one or more consecutive days followed by one or more consecutive days of rest on which the compound is not administered.

Within this embodiment, the invention encompasses the method wherein the intermittent dosing regimen comprises a repeating cycle of compound administration on 1 to 3 consecutive days followed by at least 4 days of rest.

Also within this embodiment, the invention encompasses the method wherein the compound is administered on 3 consecutive days followed by 4 days of rest.

Also within this embodiment, the invention encompasses the method wherein the compound is administered on 1 day followed by 6 days of rest.

The disease involving deposition of Aβ in the brain is typically Alzheimer's disease (AD), cerebral amyloid angiopathy, hereditary cerebral haemorrhage with amyloidosis, Dutch-type (HCHWA-D), multi-infarct dementia, dementia pugilistica or Down syndrome, in particular AD.

The term "intermittent dosing regimen" refers to repeating cycles of drug administration in which the drug is administered on one or more consecutive days ("days on") followed by one or more consecutive days of rest on which the drug is not administered ("days off"). The cycles may be regular, in that the pattern of days on and days off is the same in each cycle, or may be irregular, but regular cycles in which the drug is administered on the same weekday(s) are more convenient for the patient.

For use in medicine, the compound of the invention may be in the form of a pharmaceutically acceptable salt. Other salts may, however, be useful in the preparation of the compounds of formula I or of their pharmaceutically acceptable salts. Suitable pharmaceutically acceptable salts of the compounds of this invention include base addition salts which may, for example, be formed by mixing a solution of the compound according to the invention with a solution of a pharmaceutically acceptable base such as-alkaline earth metal salts such as sodium or magnesium salts; and salts formed with suitable organic bases, such as amine salts (including pyridinium salts) and quaternary ammonium salts. Suitable pharmaceutically acceptable salts of the compounds of this invention also include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid.

The invention is intended to include any and all crystalline, polymorphic and/or hydrated forms of the compound of the invention or any pharmaceutically acceptable salt thereof. The invention is also intended to include all enantiomeric forms of the compound, either as homochiral compounds or as mixtures of enantiomers in any proportion.

The compound of the invention may be administered in the form of a pharmaceutical composition comprising the active ingredient and a pharmaceutically acceptable carrier. Preferably the composition is in unit dosage form such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. Most suitably, the compound of the invention is administered orally in the form of tablets or capsules. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing the compound of the invention. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing a predetermined amount of the active ingredient, e.g. from 0.1 to about 500 mg of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

Optimum dosage levels will vary according to a number of factors, notably the particular intermittent regimen selected, the weight of the patient and the severity of the disease, and may be determined in each instance by protocols well-known to those skilled in the art. Generally speaking, the individual doses to be administered on an intermittent regimen in accordance with the invention will be greater than the individual doses that would be administered on a continuous regimen to give the equivalent therapeutic effect.

A specific example of a method in accordance with the invention is administration of a daily dose of 750-1500 mg of the compound of the invention, in particular 1000 mg, on a cycle of 1 day on followed by 6 days off. A further example is administration of a daily dose of 250-500 mg of the compound of the invention, in particular 350 mg, on a cycle of 3 days on followed by 4 days off.

Intermittent dosing of Example 1 as taught herein may be combined with conventional administration of one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin and atorvastatin, and compounds which are reported to inhibit the aggregation of Aβ or otherwise attenuate its neurotoxicity, such as clioquinol (Gouras and Beal, *Neuron*, 30 (2001), 641-2), 3-aminopropane-1-sulfonic acid (also known as tramiprosate or Alzhemed™), phytic acid derivatives as disclosed in U.S. Pat. No. 4,847,082 and inositol derivatives as taught in US 2004/0204387.

SYNTHESIS EXAMPLE

Example 1

1,1,1-trifluoro-N-(4-[5-fluoro-2-(trifluoromethyl) phenyl]-4-{[4-(trifluoromethyl)phenyl] sulfonyl}cyclohexyl)methanesulfonamide Step 1:

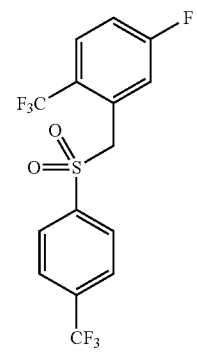

4-fluoro-1-(trifluoromethyl)-2-({[4-(trifluoromethyl) phenyl]sulfonyl}methyl)benzene Sodium sulfite (102 g, 809 mmol) was added to sodium phosphate, dibasic (58 g, 409 mmol) and water (550 ml). 4-(trifluoromethyl)benzenesulfonyl chloride (100 g, 409 mmol) and dioxane (65 ml) were then added to the reaction mixture. The reaction was heated to reflux. After 75 min, the reaction was cooled slightly and a solution of 2-trifluoromethyl-5-fluoro-benzyl bromide (75 g, 292 mmol) in ethanol (95 ml) were added and the mixture was refluxed for 1 hr. The reaction was diluted with water (400 ml) and cooled to 0° C. for 1 hr. The reaction mixture was filtered and the solid was washed with water (2×400 ml) and then with heptane (200 ml). The residue was dried under vacuum to a constant weight and carried to the next step without further purification.

$^1$H NMR (600 MHz, CDCl$_3$) δ 7.82 (d, j=8.3 Hz, 2H), 7.74 (d, J=8.4 Hz, 2H), 7.61 (dd, J=8.8, 5.4 Hz, 1H), 7.57 (dd, J=9.1, 2.5 Hz, 1H), 7.21-7.11 (m, 1H), 4.53 (s, 2H).

Step 2:

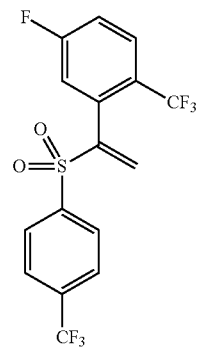 [SMILES: C=C(c1cc(F)ccc1C(F)(F)F)S(=O)(=O)c1ccc(C(F)(F)F)cc1]

1-[5-fluoro-2-(trifluoromethyl)phenyl]ethenyl 4-(trifluoromethyl)phenylsulphone 4-fluoro-1-(trifluoromethyl)-2-({[4-(trifluoromethyl)phenyl]sulfonyl}methyl)benzene (201.5 g, 522 mmol) was dissolved in DMF (1100 ml). Acetic anhydride (75 ml, 795 mmol) was added over about 3 min. The reaction was heated to 60° C. and stirred at 60° C. for 1.5 hr. A second portion of acetic anhydride (105 ml, 1113 mmol) was added dropwise over 1 hr and the reaction was heated at 60° C. for another 5.4 hr. Another portion of acetic anhydride (30 ml) was added and heated for another 5 hr at 60° C. The next day another 10 ml of acetic anhydride was added and heated to 70° C. for 2 hr. The reaction was then cooled to room temperature, water was added dropwise over 30 min. The suspension was cooled to 20° C. and filtered. The residue was washed with water (1×500 ml, and 2×250 ml). The compound was initially dried under vacuum at room temperature and then at 50° C. to a constant weight to provide 1-[5-fluoro-2-(trifluoromethyl)phenyl]ethenyl 4-(trifluoromethyl)phenylsulphone.

$^1$H NMR (500 MHz, CDCl$_3$) δ 7.78 (d, J=8.1 Hz, 2H), 7.70 (d, J=8.1 Hz, 2H), 7.65-7.59 (m, 1H), 7.40 (d, J=8.9 Hz, 1H), 7.22 (t, J=8.0 Hz, 1H), 6.87 (s, 1H), 6.08 (s, 1H). MS calculated 421.3 [M+Na]+, exp 421.1 [M+Na]+.

Step 3:

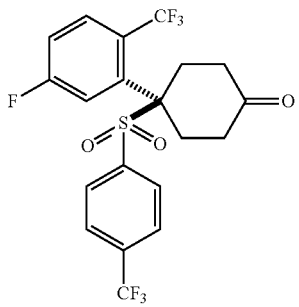

4-[5-fluoro-2-(trifluoromethyl)phenyl]-4-[4-(trifluoromethyl)phenyl]sulfonyl)cyclohexanone 1-[5-fluoro-2-(trifluoromethyl)phenyl]ethenyl 4-(trifluoromethyl)phenylsulphone (127.4 g, 320 mmol) and 2-(trimethylsiloxy)-1,3-butadiene (127.4 g, 895 mmol) were combined in a 500 ml round bottom flask flushed with nitrogen and fitted with a condenser and then placed in a 130° C. preheated oil bath. The reaction was stirred at 130-132° C. for 5 days and then transferred with toluene to a larger round bottom to concentrate. Ethyl acetate (1 L) and 1 N HCl (200 ml) were added and the reaction was stirred at room temperature for 1 hr. First the insoluble material was filtered and then the layers were separated. The organic layer was washed with brine, dried over MgSO$_4$, filtered and concentrated. The crude reaction mixture was dissolved in CH$_2$Cl$_2$ and purified by column chromatography on silica gel, eluting with ethyl acetate/heptane to provide 4-[5-fluoro-2-(trifluoromethyl)phenyl]-4-{[4-(trifluoromethyl)phenyl]sulfonyl}cyclohexanone.

$^1$H NMR (500 MHz, CDCl$_3$) δ 7.92 (dd, J=9.0 Hz, 6.0, 1H), 7.73 (d, J=8.3 Hz, 2H), 7.63 (d, J=8.2 Hz, 2H), 7.47 (dd, J=11.2, 2.4 Hz, 1H), 7.32-7.27 (m, 1H), 3.02 (dd, J=16.1, 3.5 Hz, 2H), 2.67 (td, J=14.2, 3.8 Hz, 2H), 2.56 (d, J=16.5 Hz, 2H), 2.32-2.21 (m, 2H). MS calculated 491.4 [M+Na]+, exp 491.0 [M+Na]+.

Step 4:

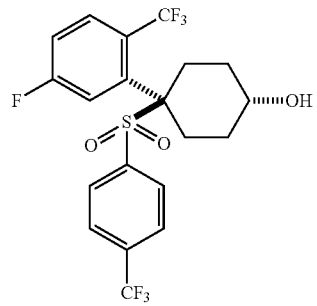

4-[5-fluoro-2-(trifluoromethyl)phenyl]-4-{[4-(trifluoromethyl)phenyl]sulfonyl}cyclohexanol A 1 L 3-neck round bottom flask equipped with a nitrogen bubbler, thermocouple, stir bar and condenser was charged with 4-[5-fluoro-2-(trifluoromethyl)phenyl]-4-{[4-(trifluoromethyl)phenyl]sulfonyl}cyclohexanone (45 g, 96 mmol) in ethanol (464 ml). Next sodium borohydride (9.67 g, 256 mmol) was added and the reaction was stirred for 30 min. The reaction was quenched by adding HCl (200 ml, 2N) slowly over 10 minutes and then the reaction was poured into HCl (2 L, 2N) and extracted with ethyl acetate (3×1 L). The organic layers were washed with brine, dried over MgSO$_4$, filtered and concentrated to provide 4-[5-fluoro-2-(trifluoromethyl)phenyl]-4-{[4-(trifluoromethyl)phenyl]sulfonyl}cyclohexanol.

$^1$H NMR (600 MHz, DMSO) δ 8.01 (dd, J=9.0, 6.2 Hz, 1H), 7.92 (d, J=8.3 Hz, 2H), 7.64 (d, J=8.1 Hz, 2H), 7.54-7.46 (m, 1H), 7.35 (dd, J=11.9, 2.4 Hz, 1H), 4.54 (d, J=5.1 Hz, 1H), 3.43 (dt, J=15.6, 5.3 Hz, 1H), 2.71 (d, J=48.9 Hz, 2H), 1.97 (t, J=13.3 Hz, 2H), 1.80 (d, J=20.4 Hz, 2H), 0.91 (d, J=52.4 Hz, 2H). MS calculated 491.4 [M+Na]+, exp 491.0 [M+Na]+

Step 5:

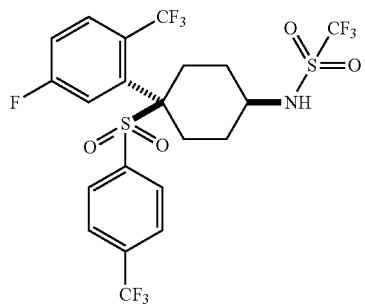

1,1,1-trifluoro-N-(4-[5-fluoro-2-(trifluoromethyl)phenyl]-4-{[4-(trifluoromethyl)phenyl]sulfonyl}cyclohexyl)methanesulfonamide A 2 L 3-neck round bottom flask equipped with a nitrogen bubbler, thermocouple, stir bar, heating mantle and condenser was charged with 4-[5-fluoro-2-(trifluoromethyl)phenyl]-4-{[4-(trifluoromethyl)phenyl]sulfonyl}cyclohexanol (94.7 g, 201 mmol) in THF (1 L). Trifluoromethanesulfonamide (45.0 g, 302 mmol) and triphenylphosphine (79 g, 302 mmol) were added, followed by DIAD (0.059 L, 302 mmol,) which was added dropwise over 20 min. The reaction was heated to 60° C. and stirred for 18 hrs at 60° C. The reaction was concentrated and dissolved in $CH_2Cl_2$ and purified by column chromatography on silica gel, eluting with ethyl acetate/heptanes to provide 1,1,1-trifluoro-N-(4-[5-fluoro-2-(trifluoromethyl)phenyl]-4-{[4-(trifluoromethyl)phenyl]sulfonyl}cyclohexyl)methanesulfonamide.

$^1$H NMR (500 MHz, cdcl3) δ 7.84 (dd, J=9.0, 6.1 Hz, 1H), 7.67 (d, J=8.4 Hz, 2H), 7.51 (d, J=8.1 Hz, 2H), 7.34 (dd, J=11.4 Hz, 2.2, 1H), 7.25-7.21 (m, 1H), 5.84 (d, J=7.7 Hz, 1H), 3.79-3.73 (m, 1H), 2.77-2.53 (m, 4H), 2.19-2.05 (m, 2H), 1.79-1.65 (m, 2H). MS calculated 623.5 [M+Na]+, exp 623.7 [M+Na]+

Biological Activity

Assays to determine the biological activity of the compounds of the invention are described as follows:

APP Processing (Assay Quantitates Secreted Aβ Analytes from Cell Lines):

The effect of compounds on the abundance of Aβ40 and Aβ42 peptides generated from SH-SY5Y cells expressing amyloid β protein (SP4CT cells) was determined by an AlphaLisa™ assay. Analogous to an ELISA assay, generation of signal in this AlphaLisa™ assay requires "donor" and "acceptor" beads to be brought in close proximity by specific antibody recognition of either Aβ40 or Aβ42 peptides. The assay was accomplished by removing media from compound-treated SP4CT cells to two different microplates, followed by the addition of donor beads conjugated with streptavidin binding a biotinylated anti-amyloid β monocolonal antibody (clone 408). Acceptor beads directly conjugated with anti-Aβ40 monoclonal antibody (G210) were added to one microplate and anti-Aβ42 monoclonal antibody (12F4) acceptor beads were added to the other. Abundance of Aβ40 and Aβ42 was directly proportional to the luminescent signal generated following excitation of donor beads by laser light.

Notch Processing: (Assay Quantitates Notch Intracellular Domain Release in Cell Lines):

A "split-luciferase" assay is used to measure inhibition of gamma secretase-dependent cleavage of the Notch protein. In this assay, HeLa cells were made to express a Notch protein lacking its extracellular domain (NotchΔE) fused to an N-terminal fragment of luciferase. The same cells also expressed a C-terminal fragment of luciferase fused to the immunoglobulin J kappa recombination signal sequence binding protein (RBP). Upon NotchΔE cleavage by gamma secretase, a Notch intracellular domain (NICD)-N terminal luciferase protein is generated which translocates to the nucleus and binds the RBP-C terminal luciferase fusion, bringing two independently nonfunctional halves of luciferase together to form a functional luciferase enzyme. The activity of luciferase in these cells is directly proportional to the amount of gamma secretase-cleaved Notch. Luciferase activity is determined by the standard techniques of luciferin addition to lysed cells and measurement of total luminescence.

ICD Transactivation (Assay Quantitates Intracellular Domain Release of a Panel of γ-Secretase Substrates in Cell Lines)

A Firefly luciferase based transactivation assay is used to measure inhibition of ε/S3-site cleavage of γ-secretase substrates. This assay involves the use of chimeric substrates harboring a GAL4/VP16 (GVP) transactivation domain fused to the intracellular domain (ICD): APP-GVP, NotchΔE-GVP, E-cadherin-GVP and CD44-GVP. Upon cleavage and release of ICDs, the GVP domain drives the expression of the luciferase gene under the control of the UAS promoter. In this assay, HEK cells were transiently co-transfected with the chimeric substrate along with a UAS promoter driven luciferase and β-galactosidase (transfection control). Upon cleavage by γ-secretase, the released ICD-GVP translocates to the nucleus to drive the expression of the UAS-luciferase gene. The activity of luciferase in these cells is directly proportional to the amount of γ-secretase-cleaved ICDs. Luciferase activity is determined by the standard techniques of luciferin addition to lysed cells and measurement of total luminescence. In addition, to account for the differences in transfection efficiencies an absorbance based β-galactosidase enzyme assay is performed to normalize the luminescence read-out.

Assessing Full Length γ-Secretase Substrates (Assay Qualitatively Assesses the Processing of a Panel of γ-Secretase Substrates)

To examine the effect of compounds on γ-secretase activity against other substrates, four HEK 293 stable cell lines overexpressing one of the following type I membrane proteins: CD43, CD44, E-Cadherin and SCN2b with a C-terminal V5 tag, were generated. Cells are plated and treated overnight with titrated compound and the phorbol ester, TPA. Since all of the proteins undergo regulated membrane proteolysis characterized by an initial ectodomain shedding event followed by the intramembraneous cleavage of the C-terminal fragment (CTF) by γ-secretase, TPA induces the initial cleavage event producing the substrate for γ-secretase. The effect of compounds on γ-secretase activity in relation to these substrates is measured by tracking the processing of the V5 tagged CTFs by Western blot analysis. Accumulation of the CTFs indicates inhibition of γ-secretase activity.

In Vitro APP Processing (Assay Quatitates Aβ Analytes Generated from a Recombinant APPC100Flag Substrate Incubated with Semi-Purified γ-Secretase)

The effect of compounds on the abundance of Aβ40 and Aβ42 peptides generated from exogenous C100Flag substrate by semi-purified γ-secretase was determined by MESO Scale ELISA. Generation of signal in this MESO Scale assay requires an anti-amyloid monoclonal antibody (clone 408) conjugated with streptavidin to bind to a biotin-coated plate. Specific [Ru(bpy)3]2+-labeled monoclonal antibodies for either Aβ40 (G210) or Aβ42 (12F4) subsequently generate an electrochemiluminescence signal upon electrochemical stimulation. The assay was accomplished by incubating compound, C100Flag substrate and CHAPSO-solubilized P2 membranes from HeLa cells or brains of mouse, rat, or dog. The reaction was then transferred to two different biotinylated microplates for detection of either Aβ40 or Aβ42.

In Vitro Notch Processing (Assay Qualitatively Assess Notch Intracellular Domain Generation from Recombinant NotchΔE100Flag Substrate Incubated with Semi-Purified γ-Secretase)

In an analogous manner, Notch processing can be monitored using the same method as the C100Flag in vitro assay but by substituting substrate for N100Flag. A polyclonal biotin-conjugated anti-DYKDDDDK antibody was used as capture antibody while a polyclonal [Ru(bpy)3]2+-labeled cleaved Notch1 antibody was used to detect NICD.

Pharmacokinetics

Pharmacokinetic parameters were determined in Sprague Dawley rats, Beagle dogs and Rhesus monkeys by dosing the compounds intravenously (IV) or orally (PO). A dose of 0.25 mg/kg was administered either IV or PO to each subject with a dosing solution of 0.25 mg/ml in a 30:70 v/v mixture of PEG400:40% Captisol®. Plasma samples were collected at 5 min. (IV only), 15 min., 30 min., 1 h, 2 h, 4 h, 6 h, 8 h, 24 h, 48 h, 72 h, 96 h, 120 h, 144 h, and 168 h. Samples were analyzed by LC-MS/MS (API5000™) to determine the concentration in plasma. Briefly, 50 µL plasma was precipitated with 200 μL acetonitrile containing an appropriate internal standard. Samples were filtered, 500 μL of water was added to each sample and 10 μL of this was injected on a $C_{18}$ column (2.0 mm×30 mm, 3 μm particle size) and eluted using a gradient LC method with water containing 0.1% formic acid as the aqueous mobile phase, and acetonitrile containing 0.1% formic acid as the organic phase. Electrospray ionization with multiple reaction monitoring was used for MS/MS detection. Plasma concentration of the compounds was determined using a standard curve that was prepared similar to the samples in the respective matrix. Non-compartmental analysis was performed using Watson 7.2 to generate the PK parameters.

Results

Biological data for Example 1 is shown in the following table. Comparative data is also provided for Example 62 described in U.S. Pat. No. 6,890,956, granted May 10, 2005, and MRK-560 described in Best et al., *J. Pharmacol. Exp. Ther.*, 317:786-790, 2006 and Best et al, *J. Pharmacol. Exp. Ther.*, 320:552-558, 2007.

| | Example 62 from U.S. Pat. No. 6,890,956 | | MRK-560 structure | | Example 1 | |
|---|---|---|---|---|---|---|
| Tissue autonomous (nM) | Aβ40 | Aβ42 | Aβ40 | Aβ42 | Aβ40 | Aβ40 |
| *In vitro assays* | | | | | | |
| Mouse | NA | NA | 0.8 | 0.4 | 2.4 | 0.8 |
| Rat | NA | NA | 1.0 | 0.4 | 1.4 | 0.3 |
| Dog | NA | NA | 5.2 | 1.3 | 1.5 | 0.5 |
| *Cell based assays* | | | | | | |
| SY5Y (nM) | 0.99 | | 0.72 | 0.51 | 1.4 ± 0.9 | 1.2 ± 0.5 |
| HeLa Notch (nM) | 154.4 | | 111.7 | | 518.5 | |
| Notch/Aβ40 | 156 | | 155 | | 370 | |
| *PK data* | | | | | | |
| Rat Cl (ml/min/kg) | 5.9 | | 2.2 | | 3.4 | |
| AUC (Norm)$_{(0-x)}$ (μM*h*kg/mg) | 6.0 | | NA | | 8.7 | |
| t 1/2 | 101 | | 26 | | 126 | |
| % F | 116 | | 67 | | 64 | |
| Dog Cl (ml/min/kg) | 0.383 | | 4.7 | | 0.234 | |
| AUC (Norm)$_{(0-x)}$ (μM*h*kg/mg) | 49.5 | | 1.1 | | 99 | |
| t 1/2 | 254 | | 18 | | 713 | |
| % F | 55 | | 14 | | 84 | |
| Rhesus Cl (ml/min/kg) | NA | | 0.8 | | 0.07 | |
| AUC (Norm)$_{(0-x)}$ (μM*h*kg/mg) | | | 9.4 | | 385 | |
| t 1/2 | | | 12 | | 228 | |
| % F | | | 23 | | 84 | |

NA = Not Available

Example A

In Rhesus monkeys the PK profile showed a long duration of exposure and extended terminal phase with Example 1 at 30 mg/kg PO single dose: plasma t ½>168 hr, AUC (0-24) 138.2 uM·hr. The average daily CSF Aβ40 reduction was ~35% relative to baseline, following PO administration of 30 mg/kg over a one week period (168 hrs; 7 days). Peak lowering of ~46% was observed 24 hrs after each dose. A minimum inhibition of >25% was maintained throughout the duration of sample collection (24 hrs; day 1 to 144 hrs; day 6). Terminal phase pharmacokinetic characteristics of Example 1 in Rhesus monkey provide continuous inhibition over the course of one week achieving both an average as well as minimum reduction of CSF Aβ40 of >25%. Rhesus monkeys showed no unformed stool or other tolerability issues over the course of the study.

Example B

Example 1 was administered orally to rhesus monkeys once-weekly at a dose of 30 mpk and levels of Aβ40 and Aβ42 in the cerebrospinal fluid (CSF) were monitored. Over a 3 week period, average reductions of approximately 40% in CSF Aβ40 and Aβ42 levels were observed, relative to vehicle-treated controls, with no evidence of GI toxicity. (However, the study was terminated after 3 weeks as a result of respiratory side-effects unconnected with Notch signaling.)

What is claimed is:
1. A compound which is

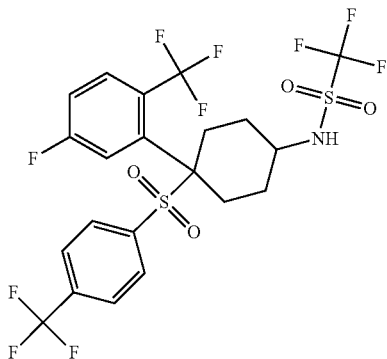 [SMILES: O=S(=O)(NC1CCC(c2cc(F)ccc2C(F)(F)F)(S(=O)(=O)c2ccc(C(F)(F)F)cc2)CC1)C(F)(F)F]

or a pharmaceutically acceptable salt thereof.

2. A compound according to claim 1 which is

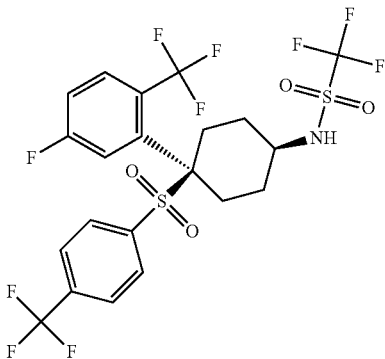 [SMILES: O=S(=O)(N[C@H]1CC[C@@](c2cc(F)ccc2C(F)(F)F)(S(=O)(=O)c2ccc(C(F)(F)F)cc2)CC1)C(F)(F)F]

or a pharmaceutically acceptable salt thereof.

3. A pharmaceutical composition comprising a compound according to claim 2 or a pharmaceutically acceptable salt thereof and a pharmaceutically acceptable carrier.

4. A method for treating a disease involving deposition of β-amyloid (Aβ) in the brain which comprises administering to a human patient in need thereof a compound according to claim 2 or a pharmaceutically acceptable salt thereof by an intermittent dosing regimen, the intermittent dosing regiment comprising repeating cycles of drug administration in which the compound is administered on one or more consecutive days followed by one or more consecutive days of rest on which the compound is not administered.

5. A method for treating Alzheimer's disease in a human patient in need thereof which comprises administering to the patient a compound according to claim 2 or a pharmaceutically acceptable salt thereof by an intermittent dosing regimen, the intermittent dosing regiment comprising repeating cycles of drug administration in which the compound is administered on one or more consecutive days followed by one or more consecutive days of rest on which the compound is not administered.

6. The method according to claim 5 wherein the intermittent dosing regimen comprises a repeating cycle of compound administration on 1 to 3 consecutive days followed by at least 4 days of rest.

7. The method according to claim 5 wherein the compound or pharmaceutically acceptable salt thereof is administered on 3 consecutive days followed by 4 days of rest.

8. The method according to claim 5 wherein the compound or pharmaceutically acceptable salt thereof is administered on 1 day followed by 6 days of rest.

* * * * *